United States Patent [19]
Hoeltke et al.

[11] Patent Number: 5,814,502
[45] Date of Patent: Sep. 29, 1998

[54] STABILIZED LIQUID MIXTURES FOR LABELLING NUCLEIC ACIDS

[75] Inventors: Hans-Joachim Hoeltke, Tutzing; Irmgard Obermaier, Penzberg; Georg Nesch, Raisting-Sölb, all of Germany

[73] Assignee: Boehringer Mannheim, GmbH, Mannheim, Germany

[21] Appl. No.: 613,997

[22] Filed: Mar. 11, 1996

Related U.S. Application Data

[63] Continuation of Ser. No. 326,967, Oct. 21, 1994, abandoned.

[30] Foreign Application Priority Data

Oct. 23, 1993 [DE] Germany .................. 43 36 266.4

[51] Int. Cl.⁶ ................. C12N 9/96; C12N 9/12; C12Q 1/68; C12Q 1/48; C12P 19/34
[52] U.S. Cl. ................. 435/188; 435/6; 435/15; 435/91.1; 435/194
[58] Field of Search ................. 435/6, 15, 91.1, 435/188, 194

[56] References Cited

U.S. PATENT DOCUMENTS

| | | | |
|---|---|---|---|
| 4,749,647 | 6/1988 | Thomas et al. | 435/5 |
| 4,762,780 | 8/1988 | Spector et al. | 435/6 |
| 4,960,690 | 10/1990 | Ellis et al. | 435/6 |
| 5,108,892 | 4/1992 | Burke et al. | 435/6 |
| 5,198,543 | 3/1993 | Blanco et al. | 536/23.2 |
| 5,256,555 | 10/1993 | Milburn et al. | 435/195 |

OTHER PUBLICATIONS

Bon Hoa et al. (1973) *J. Biol. Chem.*, 246, 4649–4654.

Weast et al. (1970) *CRC Handbook of Chemistry and Physics,* 51st Ed., The Chemical Rubber Company, p. D–188.

*Primary Examiner*—Jon P. Weber
*Attorney, Agent, or Firm*—Nikaido Marmelstein Murray & Oram LLP

[57] ABSTRACT

Stable enzyme compositions are provided in a liquid form for the enzymatic radioactive and non-radioactive labelling of nucleic acids and oligonucleotides. The mixtures preferably contain 30–60% (v/v) glycerin. At a storage temperature between $-20\,°$C. and $+4\,°$C. over a period of at least 12 months, the mixtures do not exhibit any loss of activity.

10 Claims, 3 Drawing Sheets

STABILIZED LIQUID MIXTURES FOR LABELLING NUCLEIC ACIDS

This application is a division of application Ser. No. 08/326,967 filed on Oct. 21, 1994, now abandoned.

The invention relates to compositions for labelling nucleic acids where all necessary components are present in a mixture in a liquid form. Said mixtures preferably contain glycerin.

A number of enzymatic methods is known for the preparation of radioactively (e.g. with P-32, S-35 or H-3) or non-radioactively (e.g. with digoxigenin, biotin, fluorescein, rhodamin, AMCA [=7-amino-4-methylcoumarin-3-carboxylic acid]) labelled nucleic acids (DNA or RNA). Examples include nick translation (Rigby, P. W. J. et al. (1977) J. Mol. Biol. 133, 237–251), random primed DNA labelling (Feinberg, A. P. and Vogelstein, B. (1983), Anal. Biochem. 132, 6–13; Feinberg, A. P. and Vogelstein (1984), Anal. Biochem. 137, 266–267), polymerase chain reaction (PCR) (Saiki, R. K. et al. (1985) Science 239, 487–491; Lion, T. and Haas, O. A. (1990) Anal. Biochem. 188, 335–337), 5'-end labelling, 3'-end labelling (Roychondhury, R. et al. (1979) Nucl. Acids Res. 6, 1323–1333) and in-vitro-RNA labelling (Melton, D. A. (1985) Proc. Nati. Acad. Sci. USA 82, 144–148).

The substances necessary for implementing said methods, such as enzymes, buffer, stabilizers, nucleotides, detergents etc. are commercially available.

Moreover, when DNA sequencing or RNA synthesizing is applied, inorganic pyrophosphatase may occasionally also be used to ensure a uniform intensity of the lanes by reducing product inhibition when sequencing DNA and obtain a higher yield when synthesizing RNA (Tabor, S. and Richardson, C. C. (1990) J. Biol. Chem. 265, 8322–8328; Cunningham, P. R. and Ofengard, , J. (1990), BioTechniques 9, 713–714).

However, a drawback common to all of the aforementioned enzymatic labelling methods is that the various reaction components are sold separately (or are prepared by the user) and must be stored in discrete containers. The user of the respective reagents and kits consequently has to first thaw the various components necessary for a given labelling experiment and pipette all components into the reaction vessel (i.e. the beginning of the actual experiment is delayed). In a random primed labelling experiment, for example, three additional components (nucleotides, buffered hexanucleotide mix [random primer] and Klenow enzyme) must be added individually to the labelled substrate DNA. The same also applies to the other aforementioned enzymatic reactions, requiring usually the separate addition of three components (nucleotide, buffer, enzyme) to the DNA. This procedure is not only work and time intensive but also susceptible to errors as pipetting of several relatively small volumes (1–5 $\mu$l) is difficult to reproduce. Consequently, the volumes of the yields of labelled nucleic acids greatly deviate (±50%) when several very small volumes of components are added by pipetting.

With respect to the manufacture of such reagents and kits, the presence of individual reaction components, hence, requires that kits and sets which contain several components (bottles, containers) must be manufactured, assembled, and stored. This involves an increased requirement of material, packaging, storage, and work. Also, the user has to provide the necessary storage capacity (usually a –20° C. refrigerator).

In random primed labelling procedures, it is known to use a "ready-to-go" kit (manufactured by Pharmacia). This kit contains all reaction components in a pre-mixed form and for preparing individual reaction mixtures, the components are already pre-aliquoted and dry stabilized (glassy, amorphous state). However, a disadvantage of this form is the lack of flexibility with respect to the size of the mixtures to be prepared and the time required for dissolving the glassy, amorphous components. This delays the entire procedure, rendering it less reproducible.

Another disadvantage is the following: while a random primed reaction is already quite efficient when radioactive labels are used (>60% of the radioactive nucleotide are incorporated within 30 minutes), reproducibility, reaction rate and yield could still be optimized. Spontaneous renaturing of the template DNA leads to smaller label yields as theoretically possible. Renaturing is time and temperature dependent. The addition of several components requires time and, hence, involves the risk of renaturing.

It is, therefore, an object of the invention to eliminate the aforementioned disadvantages and to offer all reaction components already pre-mixed in a liquid form so that the user only has to add an aliquot of the labelling mix of the DNA in one single pipetting step.

The object is accomplished by providing a composition which contains all the components necessary for the above listed labelling methods in an optimized mixing ratio, in a stable form, and already mixed. In a preferred manner, at least 30% (v/v) of glycerin are added to this mixture. Between 40% and 50% (v/v) of glycerin have been proven to be particularly suitable. The liquid mixtures exhibit a particularly high stability when stored between –20° C. and +4° C.

The individual components essentially include a labelling enzyme, reaction buffer, one or more nucleoside triphosphates, if necessary (a nucleoside tiiphosphate is meant to be a ribonucleoside triphosphate, deoxyribonucleoside triphosphate, or a dideoxyribonucleoside triphosphate) and other additives commonly used in enzyme reactions. Possible labelling enzymes include various DNA polymerases (Klenow, E. coli-DNA-polymerase holoenzyme, T4, Spn, Taq, Tne, Tth, Bca), RNA-polymerases (T3, T7, SP6) or terminal transferases. Further, a substance buffering at a pH of appr. 7.0, preferably a two-valent, cationic salt; generally possible nucleoside triphosphates include dATP, dCTP, dGTP, dTTP, ATP, CTP, GTP, UTP, ddATP, ddCTP, ddGTP, ddTTP or suitable modified nucleoside triphosphate, e.g. the corresponding desaza-compounds. Moreover, the mixture may contain stabilizers such as bovine serum albumin (BSA) or gelatine, spermidine, dithiothreitol (or mercaptoethanol) and/or detergents such as TRINTON® X-100 [Octophenol(ethyleneglycolether)], THESIT® [Polyoxyethylene 9 lauryl ether (Polidocanol $C_{12}E_9$)], TWEEN® (Polyoxyethylenesorbitan monolaurate 20, NP40 and BRIJ®-35 (Polyoxyethylene23 lauryl ether) or inhibitor substances, e.g. a RNase-inhibitor. Depending on the specificity of the labelling reaction, it is possible to add a random primer (particularly 12-mer, 15-mer, 9-mer, and 6-mer) or sequence-specific primers, a labelled nucleoside triphosphate, e.g. labelled with digoxigenin, biotin, fluorescein, rhodamin, aminocoumarin (AMCA) or radioactively labelled with P-32, S-35, H-3 etc.

The compositions of the invention advantageously contain the various components in certain concentration ranges.

The labelling enzyme is preferably used in a concentration range between 0.20 and 5 kU/ml, preferably between 0.5 and 2.5 kU/ml. Is has proven to be particularly advantageous to include 0.5 kU/ml of the labelling enzyme in the reaction mixture. The terminal transferase for the end label is used in the mixtures of the inventions in an amount between appr. 50 to 500 U/ml. In the PCR mix, a suitable polymerase concentration ranges between 50 and 500 U/ml, preferably 125 U/ml.

Particularly suitable buffer substances are HEPES [4-(2-Hydroxyethyl)-1-piperazinethane sulfonic acid], TRIS [2-Amino-2-(hydroxy-methyl)-1,3-propane-diol], CAPS {3-[Cyclohexylamine]-1-propane-sulfonic acid}, and TAPS (N-tris[Hydroxymethyl]methyl-3-aminipropane-sulfonic-acid) or a phosphate puffer as these substances have a buffer capacity between pH 6.5 and 8.5. The preferred concentration range is between 50 and 500 mM, a particularly suitable concentration being one of appr. 250 mM. It is also advantageous to add at least 0.1 mM of a two-valent salt, such as $MgCl_2$. Depending on the salt used, the optimal concentration range is between 25 to 100 mM and appr. 1 to 20 mM for PCR.

BSA and gelatine, preferably between 0.1 and 5 mg/ml, are contained in the reaction mixture. An advantageous concentration is one of appr. 1 mg/ml.

Spermidine is advantageously added at a concentration of up to 30 mM at a maximum, the preferred concentration being 10 mM. The concentrations of mercaptoethanol or other SH reagents can range between 0.1 and 300 mM; the preferred range for mercaptoethanol is between 5 and 50 mM and for dithiothieitol 100 to 300 mM.

Figure 1A:
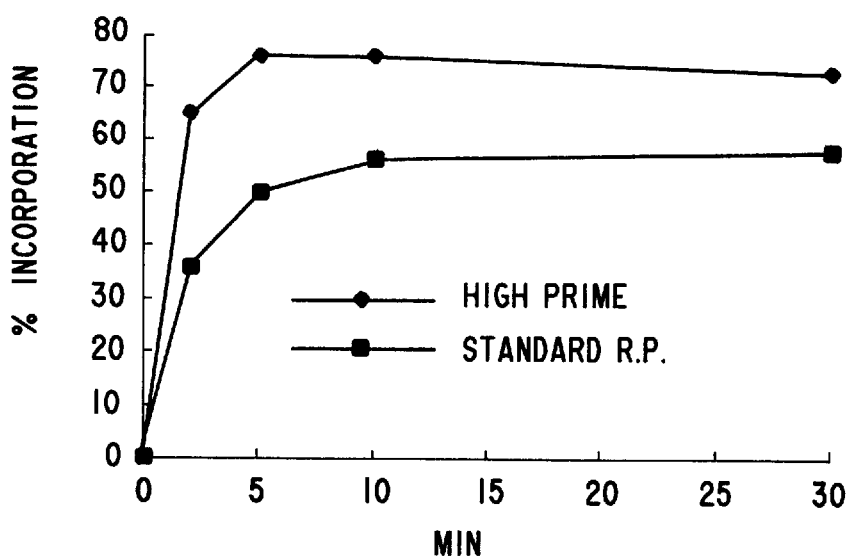
FIGS. 1a and 1b show the results of example 1 radioactive labels.

A suitable concentration range for the detergents listed above is between 0.05 and 1.0 % and particularly between 0.25 and 0.75%.

A concentration range of appr. 15 to 80 OD/ml (OD =optical density) is selected for the various random primers. Depending on the primer length, the optimal contents ranges between 30 and 60 OD/ml.

The nucleotides are advantageously added up to a concentration of appr. 20 mM; a suitable concentration ranges between 0.01 and 20 mM. Concentrations between 0.1 and 1.0 mM are particularly suitable for all reactions except the RNA labelling.

The addition of pyrophosphatase to the corresponding nucleic acid labeling or synthesis reaction brings about the additional advantage of significantly increasing rate and yield of the reaction as opposed to other known methods. 1 to 100 U/ml of enzyme are added, preferably 1–50 U/ml, particularly preferred are 1.5 U/ml. In the RNA label, 25 U/ml proved to be suitable.

A pH range between 6.5 and 8.5 and a reaction temperature between 25 and 45° C. are optimal for the composition of the invention. If a thermostable enzyme, such as Taq or Tth-DNA-polymerase, is used the optimal temperature ranges between 65° and 75° C.

It was surprising to see that the mixtures with the numerous different components are stable at all. Especially the mixture for the radioactive and non-radioactive random primed labelling methods has proven to be stable over a longer period of time (12 months). Temperatures range between −20° C. and +4° C.

However, corresponding "ready-for-use" mixtures in a stable and liquid form can also be prepared for the remaining enzymatic nucleic acid labelling methods, namely nick translation, 3'-end or 5'-end labelling, PCR reaction and, in-vitro transcription.

For the individual reactions, 4 to 20 μl of reaction solution are usually pipetted to the corresponding DNA samples. Reaction volumes of 20 to 100 μl are particularly suitable. The DNA sample can contain up to 5000 ng of DNA which can be linearized and supercoiled; and when random primed labelling is used between 100 and 70000 bases (b) long.

The following examples illustrate the invention in greater detail.

EXAMPLE 1

High Prime for radioactive DNA-label a) Composition 5x Mix (High Prime) for radioactive labels 250 mM Hepes, pH 7.0

50 mM $MgCl_2$ 0.5 mM DTE 10 mM spermidine 0.125 mM for each dATP, dGTP, dTTP 0.5% TRITON® X-100

2.5 U/ml inorganic pyrophosphatase 1 mg/ml bovine serum albumin, mol. biol.

31.4 OD/ml random primer

1000 U/ml Klenow polymerase

45% (v/v) glycerin b) High Prime Reaction as compared to a standard random primed reaction 25 ng DNA (e.g. lambda DNA) were denatured in 11 μl sterile water in a Sarstedt reagent vessel by boiling and brief chilling on ice. After briefly centrifuging the solution, 4 μl 5 x high-prime mix and 5 μl (=50 μCi) $\alpha$-$^{32}$P dCTP (3000 Ci/mmol) were added and incubated at 37° C. Aliquots of 1 μl were taken out of the reaction mixture and after precipitation with trichloroacetic acid, the relative incorporation of radioactivity into the newly synthesized DNA was determined.

A standard random primed reaction with the BM Random Primed DNA Labelling Kit (Cat. No. 1004760) was carried out to have a reference. To accomplish this, 25 ng of DNA were denatured as described above in 9 μl water. Subsequently, 3 μl of pre-mixed dATP, dGTP and dTTP (0.166 mM of each), 2 μl of hexanucleotide mix in 10 x reaction buffer, 5 μl (=50 μCi) $\alpha$-$^{32}$P dCTP (3000 Ci/mmol) and 1 μl (=2 units) Klenow polymerase were mixed. Aliquots were taken as described above, and the incorporated radioactivity was also measured as specified above.

Figure 1B:
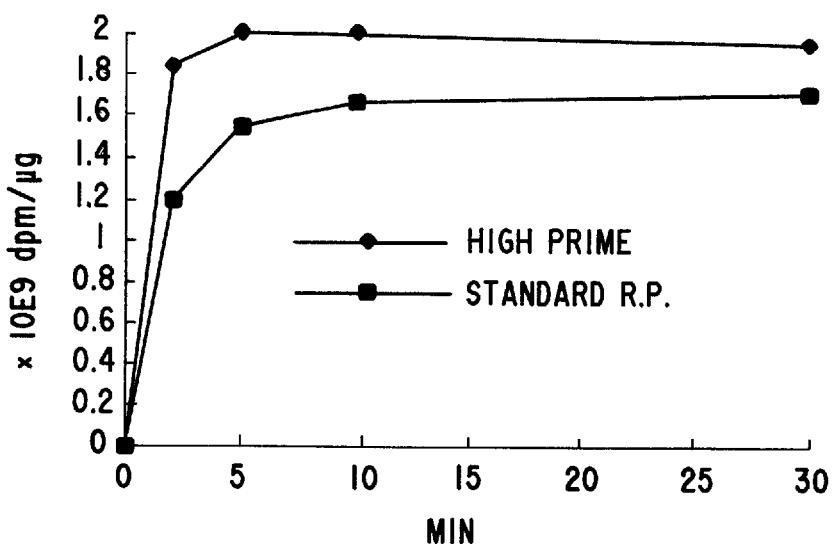

FIG. 1 shows the result of the measurement. The high prime reaction occurred faster and showed an increased incorporation of radioactivity.

| Incub. Time (min) | High Prime | Standard R.P. |
|---|---|---|
| 0 | 0 | 0 |
| 2 | 65 | 36 |
| 5 | 76 | 50 |
| 10 | 76 | 56 |
| 30 | 73 | 58 | c) Composition of 5 x high prime mix for non-radioactive labels (di goxigenin [DIG], biotin, fluorescein, rhodamin AMCA among others)

250 mM Hepes, pH 7.0

50 MgCl$_2$ 0.5 mM DTE 10 mM spermidine 1 mM for each dATP, dCTP, dGTP 0.65 mM dTTP 0.35 mM DIG-dUTP, biotin-dUTP, fluorescein-dUTP, rhodamin-dUTP or AMCA-dUTP 0.5% TRITON® X-100

2.5 U/ml inorganic pyrophosphatase 1 mg/ml bovine serum albumin, mol. biol.

31.4 OD/ml random primer

1000 U/ml Klenow polymerase

45% (v/v) glycerin

Amount of DNA: appr. 1000 ng d) DIG high prime reaction as compared to a standard DIG random primed reaction 1 µl of DNA (e.g. lambda DNA) was denatured in 16 µl of sterile water in a Sarstedt reaction vessel by boiling and brief chilling on ice. After centrifuging the solution briefly, 4 µl of 5 x DIG high prime mix were added and incubated at 37° C. To quantify it, 1 µl (=10 µCi) α-$^{32}$P DCTP were added to a parallel batch. Aliquots of 1 µl were removed from the reaction mixture at different time intervals, and the relative incorporation of radioactivity in the newly synthesized DNA was determined after percipitation with trichloroacetic acid.

A standard DIG random primed reaction was carried out with the BM DIG DNA Labelling Kit (Cat. No. 1175033). To accomplish this, 1 µg of DNA was denatured in 14 µl of water as described above. Subsequently, 2 µl of premixed DIG-dNTP labeling mix (1 mM dATP, 1 mM dATP, 1 mM dCTP, 1 mM dGTP, 0.65 mM dTTP, 0.35 mM DIG-dUTP), 2 µl of hexanucleotide mix in 10 x reaction buffer and 1 µl (=2 units) of Klenow polymerase were mixed. Another parallel batch was prepared using a radioactive tracer. Aliquots were taken as described above, and the incorporated radioactivity was also measured as specified above.

Figure 2A:
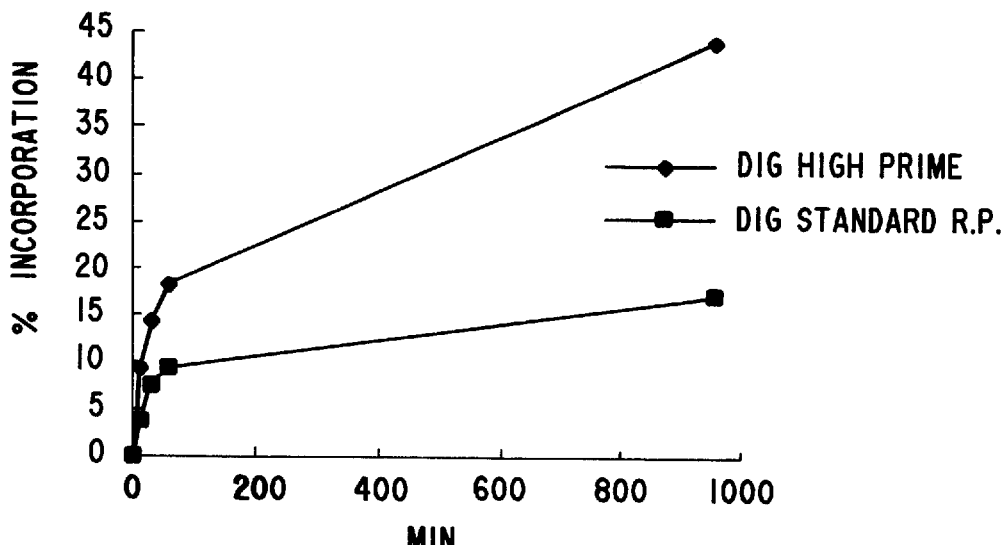
FIGS. 2a and 2b show the results of example 1 with non-radioactive labels.
Figure 2B:
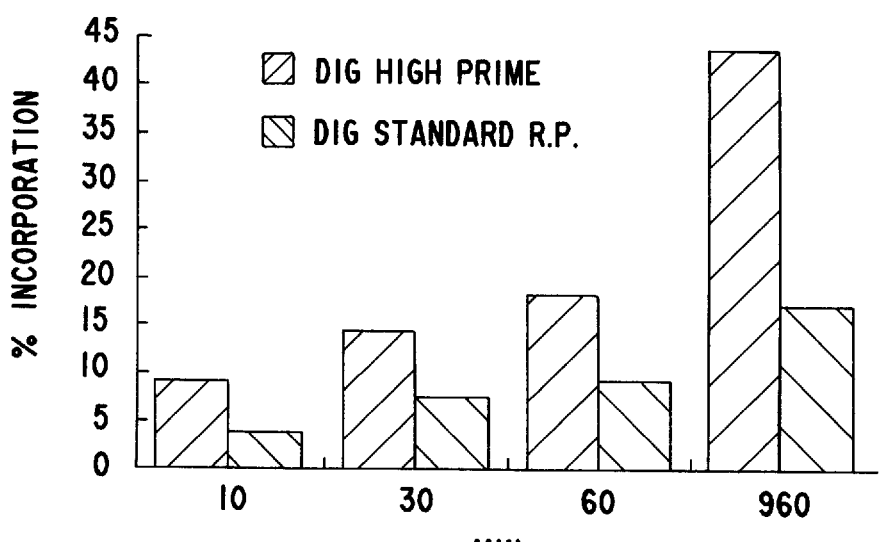
Figure 2C:
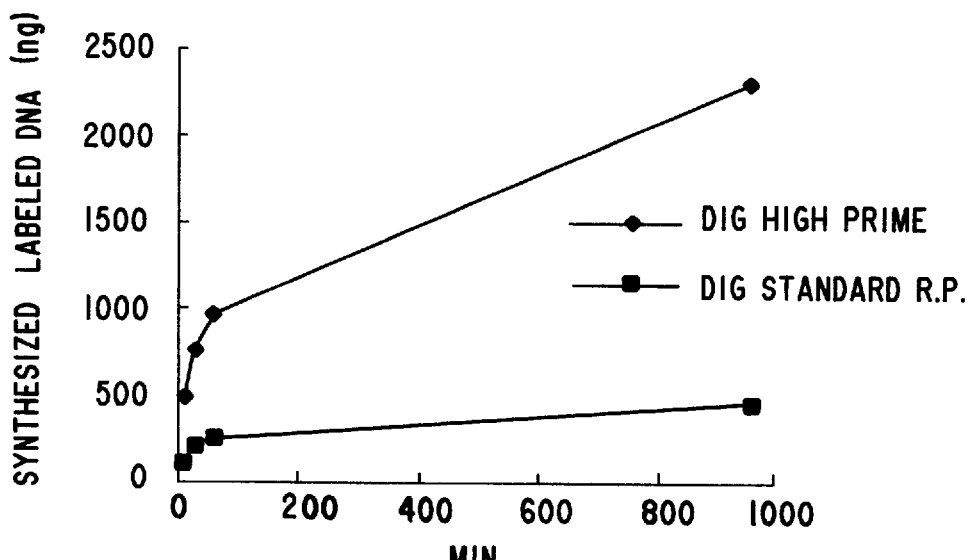
FIGS. 2c and 2d show the comparison of the high prime and the standard DIG random primed reactions.
Figure 2D:
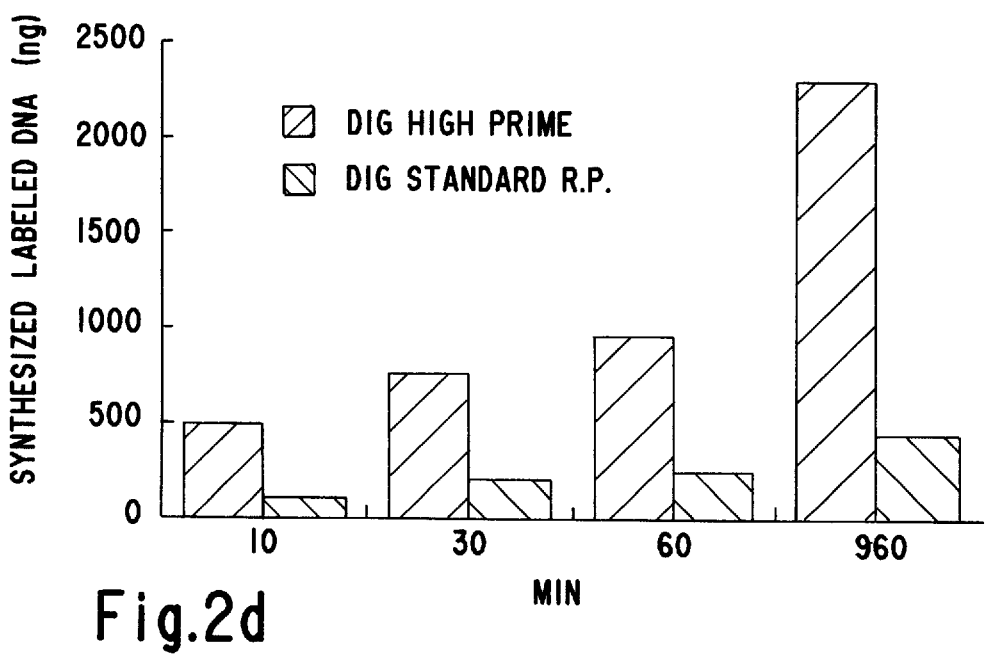

FIGS. 2a and b show the result of the measurement. The high prime reaction occurred faster and yielded a significantly increased amount of DNA as compared to the standard reaction.

| Incub. Time min | DIG High Prime % Incorp. | DIG Standard R.P. % Incorp |
|---|---|---|
| 10 | 9.3 | 3.8 |
| 30 | 14.4 | 7.6 |
| 60 | 18.2 | 9.4 |
| 960 | 43.9 | 17.2 |

| Incub. Time min | DIG High Prime Synthesis of labelled DNA (ng) | DIG Standard R.P. Synthesis of labelled DNA (ng) |
|---|---|---|
| 0 | 0 | 0 |
| 10 | 490 | 110 |
| 30 | 760 | 205 |
| 60 | 960 | 248 |
| 960 | 2310 | 454 |

The data obtained with the tracer experiments was confirmed by spot tests, where portions of 1 µl of diluted labelling reaction mixture were spotted onto a nylon membrane, fixed by UV light and detected with anti-digoxigenin alkaline phosphatase and nitro blue tetrazolium (DIG Nucleic Acid Detection Kit, Cat. No. 1175041).

A direct comparison showed that the DIG high prime reaction yielded stronger signals which proves that more labelled DNA was synthesized.

The labelling reaction was carried out using 1 µg of template-DNA, for 20 h at 37° C.; no ethanol-precipitation.

Series of spots, each with 1 µl of the corresponding dilution steps on a BM nylon membrane;

Detection with chemiluminescence (Höltke, H. J. et al. (1992) Bio Techniques 12, 104–113)

Film exposure appr. 15 min.

Example 2

Nick Translation a) Composition of 5 x mix for nick translation for a radioactive DNA label

| Components | Conc. | pH |
|---|---|---|
| Tris-HCl | 250 mM | 7.8 |
| MgCl$_2$ | 25 mM | |
| DTT | 50 mM | |
| BSA | 0.25 mg/ml | |
| Nucleotide | | |
| dATP | 0.1 mM | |
| dGTP | 0.1 mM | |
| dTTP | 0.1 mM | |
| TRITON ® X-100 | 0.5% | |
| inorg. pyrophosphatase | 2.5 U/ml | |

| Enzymes: | | Temp. |
|---|---|---|
| DNA Polymerase I | 1 kU/ml | 15° C. |
| DNase I | 0.1 µg/ml | |
| Glycerin | 45% | |
| Reaction Volume | 20 µl | |
| Amount of DNA | 100 ng | | b) High nick translations radioactive labelling reaction

4 µl of 5 x high nick translation mix and 2 µl (=20 µCi) α-$^{32}$P dCTP (3000 Ci/mol) were added to 100 ng DNA (e.g. lambda-DNA) in 14 µl of sterile water contained in a reaction vessel. Incubation was carried out at 15° C. The incorporation kinetics could be followed by removing aliquots of 1 µl at different incubation times and by determining the percentage that can be precipitated with trichloroacetic acid. The standard reaction with the BM Nick Translations Kit (Cat. No. 976776) was used as a reference according to the manufacturer's instructions. High nick translation as compared to a standard nick translation radioactive labelling reaction.

A standard nick translation reaction with the BM Nick Translation Kit (Cat No. 976 776) was carried out as a reference. To accomplish this, 100 ng DNA were mixed with 3 µl of premixed dATP, dGTP and TTP (0.133 mM of each), 2 µl of a 10x reaction buffer (0.5 mol/L TRIS-HCl; pH 7.5; 0.1 mol/L MgCl$_2$; 1 mMol/L DTT) 2 µl (=20 µCi)[α-$^{32}$P] dCTP(3000 Ci/mmol), 2 µl Enzyme mixture (containing 2 Units DNA-Polymerase 1 and 16 mUnits DNAse 1) and made up to 20 µl with sterile redist. water.

The reaction was carried out at 15° C. for 35 min. Aliquots were taken as described above and the incorporated radioactivity was measured as specified above.

The results correspond to the high prime test series: faster and higher incorporation rates of radioactivity.

c) Composition of the 5 × mix for nick translation for non-radioactive labels

| Components | Concentration |
| --- | --- |
| Tris-HCl pH 7.8 | 250 mM |
| MgCl$_2$ | 25 mM |
| DTT | 50 mM |
| BSA | 0.25 mg/ml |
| Nucleotide dATP | 1 mM |
| dCTP | 1 mM |
| dGTP | 1 mM |
| dTTP | 0.65 mM |
| DIG-dUTP or biotin-dUTP or fluorescein-dUTP or rhodamin-dUTP or AMCA-dUTP | 0.35 mM |
| TRITON ® X-100 | 0.5% |
| inorg. pyrophosphatase | 2.5 U/ml |
| DNA Polymerase 1 | 1 kU/ml |
| DNase I | 0.1 µg/ml |
| Glycerin | 45% |
| Amount of DNA | 1000 ng | d) Dig High Nick Translation: typical reaction mixture

All pipetting steps can be carried out as described under b); for a quantification, we added 1 µl dCTP (=10 µCi) for each reaction mixture.

EXAMPLE 3

PCR a) Composition of the 5 × PCR-Mix (unlabelled)

| Components | Concentration |
| --- | --- |
| Tris-HCl | 50 mM, pH 8.3 |
| TAPS | |
| KCl | 250 mM |
| Nucleotides | each 1 mM |
| dATP | |
| dCTP | |
| dGTP | |
| dTTP | |
| MgCl$_2$ | 7.5 mM |
| Stabilizers | 0.5% |
| TWEEN ® -20 or | |
| TRITON ® X-100 or | |
| THESIT ® or | |
| NONIDET ® P 40 | |
| [Ethylphenolpoly(ethyleneglycolether)$_n$] or | |
| BRIJ ® 35 or | |
| Octylglycoside | |
| Taq-polymerase | 125 U/ml |
| Glycerin | 50% |
| Reaction volume | 100 µl |
| Amount of DNA | 10–100 ng |
| Primer | 1 µM each | b) PCR Reaction without label

DNA, e.g. human genomic DNA, 100 ng, is incubated in a theimocycler with specific PCR primers, e.g. for a given human gene (cystic fibrosis, factor IX or others), 1 µM each, in 80 µl of sterile water plus 20 µl of 5 × PCR-mix. Cycle program, e.g. 1 min 95 ° C., 1 min 55 ° C., 1 min 72 ° C. etc., 30 cycles, at the end 5 min at 72 ° C. One aliquot of the reaction mixture was analyzed in an ethidium bromide agarose gel.

c) PCR for a non-radioactive label with DIG

The 5 × PCR labelling mix has the same composition as he one above, except that 0.65 mM dTTP are contained instead of 1 mM dTTP and 0.35 mM DIG-dUTP. The ratios of DIG-dUTP/dTTP can be varied such that only 0.05 mM DIG-dUTP and 0.95 mM dTTP are mixed. The PCR reaction occurs as described above. The DIG-labelled PCR product can either be used as a hybridization sample or it is transferred onto a membrane (nylon, positively charged) after gel electrophoresis and detected according to the usual DIG-detection method with color or chemiluminescence.

EXAMPLE 4

3'-end labelling a) DNA 3'-end label with radioactivity
Composition of the 5 × Mix* + 5 × potassium cacodylate*.

| Components | Concentration |
| --- | --- |
| CoCl$_2$* | 25 mM |
| Tris-HCl pH 6.6 | 125 mM |
| BSA | 1.25 mg/ml |
| Terminal Transferase | 12500 U/ml |
| Glycerin | 45% |
| Amount of DNA | 10 pmol |

5 × potassium cacodylate: 1 M*
*Note:
CoCl$_2$ and potassium cacodylate cannot be mixed in the 5 × mix.

b) Standard reaction of the radioactive 3'-end labelling

In a reaction vessel, 4 µl of 5 × mix, 4 µl of 5 × potassium cacodylate and 5 µl of α-$^{32}$P ddATP (3000 Ci/mmol) in a total volume of 20 µl are added to 10 pmol 3'-OH ends (=5 µl control DNA, pBR 322 with 0.26 mg/ml). Incubation is carried out at 37 ° C. for 60 min.

The incorporation rate was determined as in example 1 using trichloroacetic acid.

c) DIG oligonucleotide 3'-end labelling
Composition of the 5 × mix* and 5 × potassium cacodylate*

| Components | concentration |
| --- | --- |
| CoCl$_2$* | 25 mM |
| Tris-HCl pH 6.6 | 125 mM |
| BSA | 1.25 mg/ml |
| Terminal Transferase | 12500 U/ml |
| DIG ddUTP | 0.25 mM |
| Glycerin | 45% |
| Amount of oligonucleotide | 100 pmol |

5 × potassium cacodylate: 1 M* d) DIG oligonicleotide 3'-end labelling standard reaction

Corresponding to the radioactive 3'-end labelling, without $^{32}$P ddATP; Incubation was carried out for 15 min at 37 ° C.

e) DIG oligonucleotide tailing
Composition of the 5 × mix* and 5 × potassium cacodylate* (1 M)

| Components | Concentration |
| --- | --- |
| CoCl$_2$* | 25 mM |
| Tris-HCl pH 6.6 | 125 mM |
| BSA | 1.25 mg/ml |
| Terminal Transferase | 12500 U/ml |
| dATP | 2.5 mM |
| DIG-11-dUTP | 0.25 mM |
| Glycerin | 45% |
| Amount of oligonucleotide | 100 pmol | f) DIG oligonitcleolide tailing, standard reaction

Corresponding to the DIG oligonucleotide 3'-end labelling in 20 μl total volume. Incubation was carried out at 37° C. for 15 min.

EXAMPLE 5

RNA Labelling (Transcription)

a) SP6/T7/T3 transcription, radioactive RNA labeling
Composition of the 5 × mix

| Components | Concentration |
| --- | --- |
| Hepes, pH 7.6 | 400 mM |
| MgCl$_2$ | 60 mM |
| DTT | 200 mM |
| Spermidine | 10 mM |
| RNase-Inhibitor | 2.5 kU/ml |
| inorg. pyrophosphatase | 25 U/ml |
| ATP | 2.5 mM |
| GTP | 2.5 mM |
| UTP | 2.5 mM |
| SP6 RNA-Polymerase | 2000 U/ml |
| or T7 RNA-Polymerase | " |
| or T3-RNA-Polymerase | " |
| Glycerin | 45% |
| Amount of DNA | 1 μg | b) Radioactive RNA labelling by in vitro transcription, standard reaction

4μl of the 5 × mix and 5 μl of a-$^{32}$P CTP (400 Ci/mmol) in a total volume of 20 μl are added to 1 μg DNA with SP6, T7 or T3 promotor. Incubation was carried out at 37° C. for 20 min.

The incorporation rate was determined as in example 1 using trichloroacetic acid.

c) DIG RNA labelling
Composition of the 5 × mix

| Components | Concentration |
| --- | --- |
| Hepes, pH 7.6 | 400 mM |
| MgCl$_2$ | 60 mM |
| DTT | 200 mM |
| Spermidine | 10 mM |
| RNase-Inhibitor | 2.5 kU/ml |
| inorg. pyrophosphatase | 25 U/ml |
| ATP | 15 mM |
| CTP | 15 mM |
| GTP | 15 mM |
| UTP | 10 mM |
| DIG-11-UTP | 5 mM |
| SP6 RNA-Polymerase | 4000 U/ml |
| or T7 RNA-Polymerase | " |
| or T3 RNA Polymerase | " |
| Glycerin | 45% |
| Amount of DNA | 1 μg | d) DIG RNA Labelling, standard reaction as in b) without radioactivity, with an incubation time of 120 min at 37° C. The determination of the incorporation rate can be accomplished by adding 1 μl of $^{32}$P UTP tracer.

Evaluation and results correspond to example 1.

FIGS. 2 c) and d) show the comparison of the DIG high prime and the standard DIG random primed reaction, in nanograms of synthesized labeled DNA over time.

We claim:

1. A stable pre-mixed composition for synthesizing or labelling nucleic acids comprising:
   a) an enzyme which synthesizes or labels nucleic acids,
   b) reaction buffer,
   c) between 30% and 60% (v/v) glycerin, and
   d) at least one nucleoside triphosphate, wherein the composition is liquid when a) through d) are mixed together and stored at −20° C., and the composition does not exhibit a loss of enzyme activity upon storage over a period of at least 12 months at −20° C. to +4° C.

2. The composition of claim 1, wherein the enzyme is a polymerase, and further comprising at least three nucleoside triphosphates, and a random nucleic acid primer.

3. The composition of claim 2 further comprising at least one component selected from the group consisting of MgCl$_2$, dithiothreitol, spermidine, BSA, and a non-ionic detergent.

4. The composition of claim 2 further comprising at least one nucleoside triphosphate which is non-radioactively labelled.

5. The composition of claim 1, further comprising an inorganic pyrophosphatase.

6. The composition of claim 1 wherein the enzyme is selected from the group consisting of DNA polymerases, RNA polymerases, and terminal transferases.

7. A method of synthesizing or labelling nucleic acids or oligonucleotides comprising:
   a) providing initial nucleotides or oligonucleotides,
   b) mixing the composition of claim 1 with said initial nucleotides or oligonucleotides of a), and
   c) synthesizing or labelling said nucleic acids or oligonucleotides from said initial nucleotides or oligonucleotides of step a).

8. A kit containing all the components of the composition of claim 1 in one container in a ratio which is optimized for the specific synthesis or labelling reaction, and an additional component selected from the group consisting of a control and a radioactive labelling reagent in a separate container.

9. A method of stabilizing compositions used for nucleic acid synthesis or labelling, said method comprising:
   a) providing a pre-mixed composition comprising an enzyme which synthesizes or labels nucleic acids, and reaction buffer, and
   b) adding at least 30% (v/v) glycerin as stabilizer, and wherein the resulting composition does not exhibit a loss of enzyme activity upon storage over a period of at least 12 months at −20° C. to +4° C.

10. A liquid-containing vessel containing a stable pre-mixed composition for synthesizing or labelling nucleic acids comprising:
   a) an enzyme which synthesizes or labels nucleic acids,
   b) reaction buffer, and
   c) at least one nucleoside triphosphate, the vessel contents being mixed together and at a temperature of −20° C., and wherein the resulting composition does not exhibit a loss of enzyme activity upon storage over a period of at least 12 months at −20° C. to +4° C.

* * * * *